US007016030B2

United States Patent
Naulleau

(10) Patent No.: US 7,016,030 B2
(45) Date of Patent: Mar. 21, 2006

(54) EXTENDED SURFACE PARALLEL COATING INSPECTION METHOD

(75) Inventor: Patrick P. Naulleau, Oakland, CA (US)

(73) Assignee: EUV LLC, Santa Clara, CA (US)

( * ) Notice: Subject to any disclaimer, the term of this patent is extended or adjusted under 35 U.S.C. 154(b) by 319 days.

(21) Appl. No.: 10/689,171

(22) Filed: Oct. 20, 2003

(65) Prior Publication Data

US 2005/0083515 A1  Apr. 21, 2005

(51) Int. Cl.
G01N 21/00 (2006.01)
G01B 11/28 (2006.01)

(52) U.S. Cl. .............................. 356/237.2; 356/237.5; 356/630

(58) Field of Classification Search ...................... None
See application file for complete search history.

(56) References Cited

U.S. PATENT DOCUMENTS

| 5,091,650 | A | 2/1992 | Uchida et al. .............. 250/366 |
| 5,438,879 | A | 8/1995 | Reda ............................ 73/800 |
| 5,958,605 | A | 9/1999 | Montcalm et al. .......... 428/627 |
| 6,097,483 | A * | 8/2000 | Komatsu .................. 356/237.2 |
| 6,211,525 | B1 | 4/2001 | Cowham ..................... 250/484 |
| 6,218,671 | B1 | 4/2001 | Gordon et al. .............. 250/397 |
| 6,392,792 | B1 | 5/2002 | Naulleau ..................... 359/360 |
| 6,399,957 | B1 * | 6/2002 | Murata ..................... 250/559.4 |
| 6,525,829 | B1 | 2/2003 | Powell et al. ............... 356/630 |
| 6,555,828 | B1 | 4/2003 | Bokor et al. ................ 250/492 |
| 6,650,421 | B1 * | 11/2003 | Magome ..................... 356/521 |
| 2003/0067598 | A1 * | 4/2003 | Tomie ...................... 356/237.2 |

\* cited by examiner

Primary Examiner—Michael P. Stafira
(74) Attorney, Agent, or Firm—Cascio Schmoyer & Zervas

(57) ABSTRACT

Techniques for rapidly characterizing reflective surfaces and especially multi-layer EUV reflective surfaces of optical components involve illuminating the entire reflective surface instantaneously and detecting the image far field. The technique provides a mapping of points on the reflective surface to corresponding points on a detector, e.g., CCD. This obviates the need to scan a probe over the entire surface of the optical component. The reflective surface can be flat, convex, or concave.

43 Claims, 2 Drawing Sheets

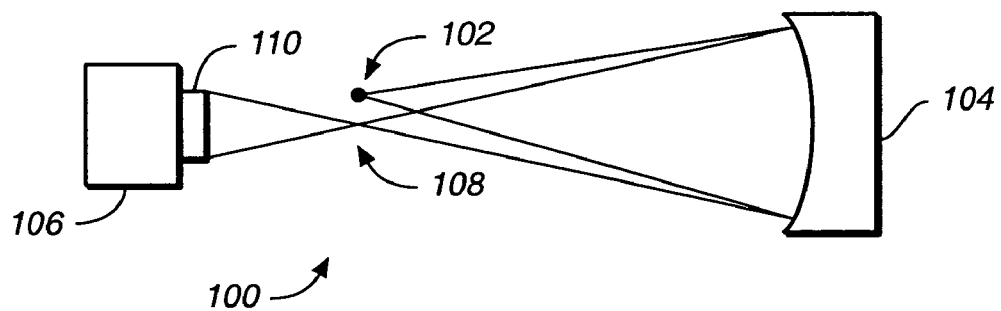
FIG._1
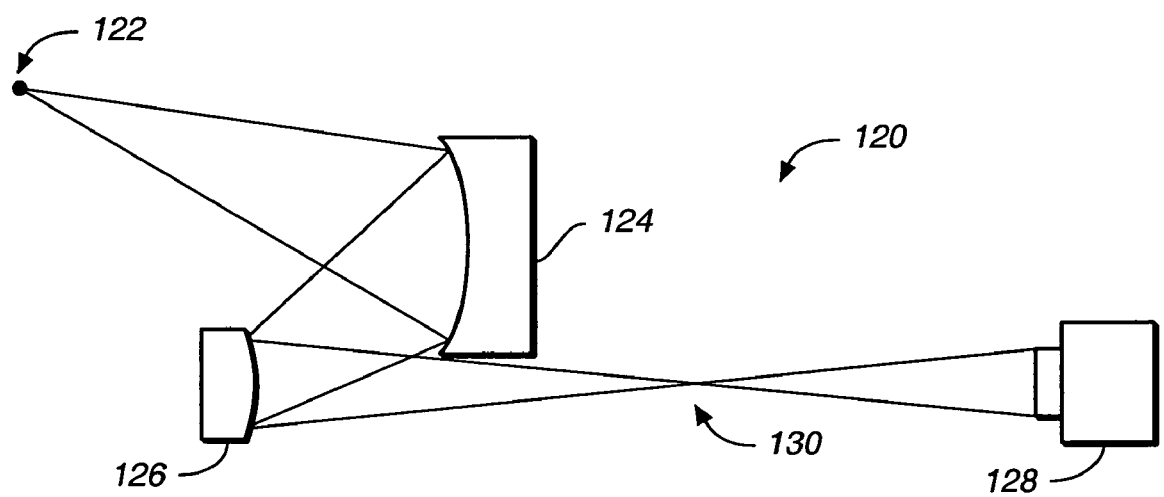
FIG._2

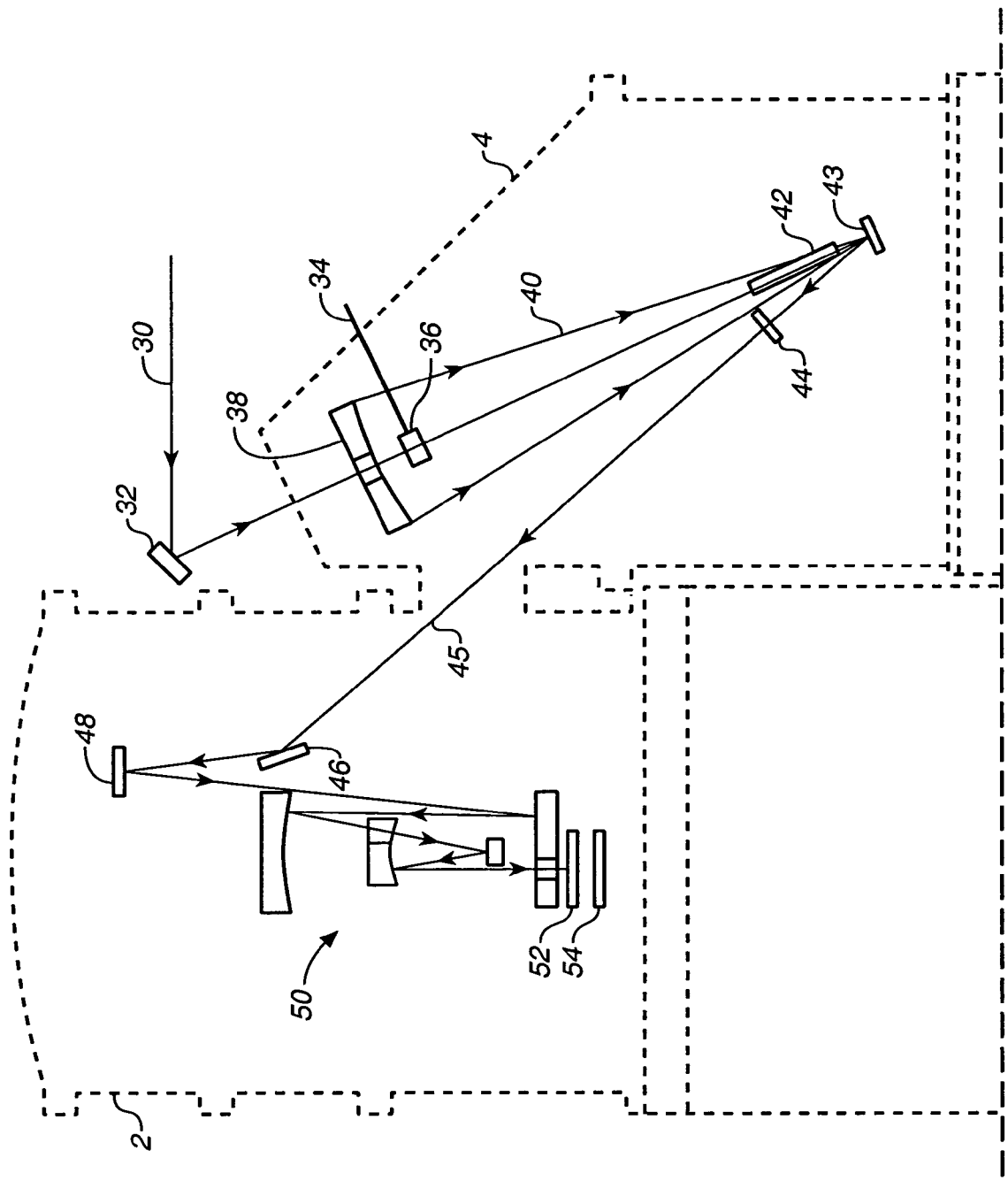
FIG._3
*(PRIOR ART)*

EXTENDED SURFACE PARALLEL COATING INSPECTION METHOD

The U.S. Government has certain rights in this invention pursuant to Contract No. DE-AC03-76SF00098 between the United States Department of Energy and the University of California for the operation of the Lawrence Berkeley National Laboratory.

FIELD OF THE INVENTION

This invention relates to methods of evaluating the reflection uniformity of an optical component and particularly to techniques for evaluating optical components having EUV reflective surfaces for used in EUV lithography.

BACKGROUND OF THE INVENTION

EUV lithography is now the leading candidate for next-generation semiconductor manufacturing at critical dimensions (CDs) of 70 nm and below. In general, lithography refers to processes for pattern transfer between various media. A lithographic coating is generally a radiation-sensitized coating suitable for receiving a cast image of the subject pattern. Once the image is cast, it is indelibly formed on the coating. The recorded image may be either a negative or a positive of the subject pattern. Typically, a "transparency" of the subject pattern is made having areas which are selectively transparent or opaque to the impinging radiation. Exposure of the coating through the transparency placed in the close longitudinal proximity to the coating causes the exposed area of the coating to become selectively crosslinked and consequently either more or less soluble (depending on the coating) in a particular solvent developer. The more soluble (i.e., uncrosslinked) areas are removed in the developing process to leave the pattern image in the coating as less soluble crosslinked polymer.

Projection lithography is a powerful and essential tool for microelectronics processing and has supplanted proximity printing. "Long" or "soft" x-rays (a.k.a. Extreme UV) (wavelength rate of 10 to 20 nm) are now at the forefront of research in efforts to achieve smaller transferred feature sizes. With projection photolithography, a reticle (or mask) is imaged through a reduction-projection (demagnifying) lens onto a wafer. Reticles for EUV projection lithography typically comprise a glass substrate coated with an EUV absorbing material covering portions of the reflective surface. In operation, EUV radiation from the illumination system (condenser) is projected toward the surface of the reticle and radiation is reflected from those areas of the reticle reflective surface which are exposed, i.e., not covered by the EUV absorbing material. The reflected radiation is re-imaged to the wafer using a reflective optical system and the pattern from the reticle is effectively transcribed to the wafer.

A source of EUV radiation is the laser-produced plasma EUV source, which depends upon a high power, pulsed laser (e.g., a yttrium aluminum garnet ("YAG") laser, or an excimer laser, delivering 500 to 1,000 watts of power to a 50 $\mu$m to 250 $\mu$m spot, thereby heating a source material to, for example 250,000° C., to emit EUV radiation from the resulting plasma. Plasma sources are compact, and may be dedicated to a single production line so that malfunction does not close down the entire plant. A stepper employing a laser-produced plasma source is relatively inexpensive and could be housed in existing facilities. It is expected that EUV sources suitable for photolithography that provide bright, incoherent EUV and that employ physics quite different from that of the laser-produced plasma source will be developed. One such source under development is the EUV discharge source.

EUV lithography machines for producing integrated circuit components are described, for example, in U.S. Pat. No. 6,031,598 to Tichenor et al. Referring to FIG. 3, the EUV lithography machine comprises a main vacuum or projection chamber 2 and a source vacuum chamber 4. Source chamber 4 is connected to main chamber 2 through an airlock valve (not shown) which permits either chamber to be accessed without venting or contaminating the environment of the other chamber. Typically, a laser beam 30 is directed by turning mirror 32 into the source chamber 4. A high density gas, such as xenon, is injected into the plasma generator 36 through gas supply 34 and the interaction of the laser beam 30, and gas supply 34 creates a plasma giving off the illumination used in EUV lithography. The EUV radiation is collected by segmented collector 38, that collects about 30% of the available EUV light, and the radiation 40 is directed toward the pupil optics 42. The pupil optics consists of long narrow mirrors arranged to focus the rays from the collector at grazing angels onto an imaging mirror 43 that redirects the illumination beam through filter/window 44. Filter 44 passes only the desired EUV wavelengths and excludes scattered laser beam light in chamber 4. The illumination beam 45 is then reflected from the relay optics 46, another grazing angel mirror, and then illuminates the pattern on the reticle 48. Mirrors 38, 42, 43, and 46 together comprise the complete illumination system or condenser. The reflected pattern from the reticle 48 then passes through the projection optics 50 which reduces the image size to that desired for printing on the wafer. After exiting the projection optics 50, the beam passes through vacuum window 52. The beam then prints its pattern on wafer 54.

As is apparent, the EUV lithography device includes a number of reflective optical components. One of the key enabling technologies for EUV lithography is the development of EUV reflective multilayer mirrors that consists of alternating thin layers of at least two refractive materials. The typical period of this structure for EUV applications is approximately 7 nm and nominally 40 to 80 periods are used. Relatively large optical systems (400 mm or larger) and masks are employed EUV lithography. Optimum performance of these resonant reflective structures requires extremely accurate thickness control of these layers over large reflective areas.

Current methods of coating characterization of single optical elements is done using discrete point reflectometry measurements at selected wavelengths. These measurements determine the reflectivity integrated over a relatively small spot on the surface of an optical element; typically these spots have diameters on the order of a few hundred microns. When information across the entire reflective surface is desired, the optical element is typically moved under the beam and the measurement is repeated at a variety of locations in a serial manner. This can be very time consuming especially when dense information is desired. Dense information is crucial to the goal of characterizing coating uniformity and failure to collect dense information significantly increases the risk of failing to detect localized coating errors on the optical component that could render the device, into which optical component is employed, unusable. The art is in need of a technique that allows the full surface to be characterized in parallel thereby enabling faster evaluation of coating uniformity characteristics.

SUMMARY OF THE INVENTION

The present invention is directed to techniques for rapidly characterizing reflective surfaces and especially for characterizing large surface multi-layer EUV mirrors. The invention is based, in part, on the discovery that illuminating the entire optical surface at the same time and detecting the image far field provides the mapping of points on the optic to corresponding points on a detector, e.g., CCD. This invention obviates the need to scan a probe over the entire surface of the optical component.

In one embodiment, the invention is directed to a method that is suited for evaluating the reflection coating uniformity of an optical component that has a concave reflective optical surface, the method includes the steps of:

(a) providing an illumination source of divergent radiation having a first wavelength;

(b) positioning the optical component so that its concave reflective optical surface transforms diverging radiation from the source of divergent radiation into a converging beam at a focused point where an image of the source of divergent radiation is created;

(c) positioning a spatially imaging radiation detector far field from the focused point of the converging beam such that substantially the entire surface of the detector is illuminated by the beam reflected from the concave surface;

(d) creating a recorded image by recording a first image that is reflected from the concave reflective optical surface to thereby geometrically map lateral positions on the concave reflective optical surface of the optical component to lateral positions of the spatially imaging detector;

(e) analyzing intensity variations across the recorded image to determine reflectivity variations across the optical surface;

(f) extrapolating reflection coating uniformity information from the reflectivity variations; and (g) optionally, repeating steps (a) through (b) one or more times as desired using divergent radiation with a different wavelength in each repetition.

In another embodiment, the invention is directed to a method for evaluating the coating uniformity of an optical component that has a convex or flat reflective optical surface, the method includes the steps of:

(a) providing an illumination source of divergent radiation having a first wavelength;

(b) positioning a concave optic which transforms the illumination source into a convergent beam;

(c) positioning the convex or flat optical component under test so that its convex or flat reflective optical surface is illuminated by the convergent beam;

(d) positioning a spatially imaging detector such that substantially the entire beam reflected from the convex or flat reflective surface is projected onto said detector;

(e) creating a recorded image by recording a first image that is reflected from the convex or flat reflective optical surface to thereby geometrically map lateral positions on the convex or flat reflective optical surface of the optical component to the lateral positions of the spatially imaging detector;

(f) analyzing intensity variations across the recorded image to determine the reflectivity variations across the optical surface;

(g) extrapolating the reflection coating uniformity information from the reflectivity variations; and (h) optionally, repeating steps (a) through (g) one or more times as desired using divergent radiation with a different wavelength in each repetition.

BRIEF DESCRIPTION OF THE DRAWINGS

FIGS. 1 and 2 illustrate techniques for inspecting concave and convex EUV mirrors, respectively; and FIG. 3 illustrates an EUV lithography device.

DETAILED DESCRIPTION OF THE PREFERRED EMBODIMENTS

FIG. 1 illustrates a system 100 for testing an optical component having a concave reflective surface such as concave EUV mirror 104. The system employs a divergent EUV source (coherent or incoherent) 102 that illuminates an area on the optic under test. EUV lithography devices typically employ concave mirrors that have EUV reflective surfaces having surface areas of at least 10 $mm^2$ and typically between 80 $mm^2$ and 80,000 $mm^2$. The inventive technique inspects the entire EUV reflective surface of the mirror by illuminating the entire EUV reflective surface at one instance without having to scan the illumination across the reflective surface.

In the case of a coherent source, the divergence could be provided by, for example, pinhole diffraction or scatter-plate diffusion. The illumination source point position should be placed such that the concave optic transforms the diverging illumination to converging as shown. Preferably, the source position should match the design source position for the optic under test. An EUV-sensitive charge coupled detector (CCD) camera 106 is placed in the far field of the re-imaged source or convergent point 108 created by the optic under test. The distance from the re-imaged source 108 to the position the CCD depends on the numerical aperture of the optic. Preferably the distance is chosen such that the illumination completely covers the EUV-sensitive surface 110.

Placing the CCD 106 far from the re-imaged source 108 leads to a geometric mapping between lateral position on the mirror surface of optic 104 and lateral position on the CCD. Observing the detected intensity variations across the CCD thereby yields information on reflectivity variations across the mirror surface. This information is acquired in parallel without the need for scanning. Even more information about the coatings can be gathered by recording several mirror reflectivity images as a function of illumination wavelength. Because EUV coatings are resonant reflective structures, multilayer thickness errors are strongly manifested as wavelength dependent reflectivity effects. This additional data also facilitates the separation of coating and substrate induced reflectivity losses.

In general, distortion-free mapping from the mirror surface to the CCD is extremely difficult to achieve and requires perfect placement of the source point. Although this poses a problem in the realm of interferometric metrology intended for mirror-surface-figure polishing, it is not of significant concern for the coating characterization where the results is used primarily as a pass-fail test and for process quality control. Since the coating characterization results are not directly fedback for corrections to be made on a test piece being characterized, there is typically no requirement for accurate mapping in using the inventive technique. In this vein, with the inventive method only amplitude measurements are needed, that is, the method does not require the phase to be measured.

A potential problem arises if the source point 102 must be placed relatively far from the ideal point or the mirror coating of the optic is graded to account for varying angles of illumination across an extended field. In these situations, the design angles of the coating will not be honored by the test-illumination angles and reflectivity variations will be induced due to this effect. These variations, however, can be quantitatively predicted and corrected for through calibration. The real point of the measurement is to determine the difference between what is measured and what is expected from an ideal coating. Using the illumination wavelength tuning described above also serves as an additional point from which to make the ideal-to-measured comparison, revealing possible errors in the coating.

Another way to avoid this potential problem is to compare the reflectivity map of the test piece to a reference piece of identical design that has been independently characterized, using for example, the slower scanning reflectometry method.

The EUV-sensitive device 105 can comprise an EUV-sensitive scintillator plate such as single crystal yttrium aluminum garnet (YAG) or $Bi_4Ge_3O_{12}$ (BGO) that is re-imaged using visible light optics to a conventional visible-light CCD.

The above describes the characterization of a concave optic, however, there are many cases where convex or flat optics might also need to be characterized. One case of particular interest is to inspect flat multilayer-coated EUV-lithography mask blanks. In these instances, it is not possible to simply illuminate the surface with a diverging beam since the beam would continue diverging and parts of interest would typically be much larger than commercially available CCD arrays, making it impossible to get a complete mapping of all the parts onto the CCD. In these cases, a converging illumination beam would be desired.

As show in FIG. 2, this could be achieved in system 120 by combining a diverging source 122, as described above, with a source converger concave optic 124 and EUV CCD detector 128. The concave optic 124 reflects the diverging beam and creates a converging beam with a stronger convergence than the divergence produced by the optic under test 126 so a converging beam comes off the diverging mirror of optic 126. The detector 128 is positioned in the far field of the composite image 130 to achieve the mapping of reflectivity versus position. As is apparent, system 120 can be employed to inspect concave reflective surfaces of optical components as well.

Any effects induced by the source-converger optic 124 could be measured and calibrated out of the system. In the case where the convex optic under test 126 is ultimately to be used as part of a multi-element optical system, the converger optic 124 can simply be a copy of a previously tested optic (optic 104 of FIG. 1) in the optical chain. Again this could serve as an extremely rapid pass-fail test. The coated optic would be placed in the test system and the recorded intensity distribution versus wavelength would be compared to stored maps either measured from a known good optic or predicted from calculations. The pass-fail criteria would depend on the design specifications of the optic under test.

EUV lithography devices typically employ convex or flat mirrors that have EUV reflective surfaces having surface areas of at least 10 $mm^2$ and typically between 800 $mm^2$ and 80,000 $mm^2$. Again, the inventive technique can inspect the entire EUV reflective surface of the mirror by illuminating the entire EUV reflective surface at one instance without scanning the illumination across the reflective surface.

The invention is particularly suited for inspecting EUV reflective mirrors and other optical components with EUV reflective surfaces that are employed in EUV lithography. EUV reflective surfaces typically comprise multilayer stacks that are deposited on substrate surfaces. Methods for fabricating multilayer stacks are known in the art.

Each multilayer reflection stack is designed to reflect at the wavelength of interest and is formed of alternating layers of two or more materials. Preferred materials include, for example, molybdenum (Mo), silicon (Si), tungsten (W), carbon (C), beryllium (Be), ruthenium (Ru), $B_4C$, $Mo_2C$, titanium (Ti), and vanadium (V). Preferred stacks are formed from alternating layers of two materials that are selected from the following list of seven pairs: Mo—Si, W—C, Mo—Be, Ru—$B_4C$, $Mo_2C$—Si, Ti—C, V—C. Alternating layers of Mo and Si are particularly preferred for EUV applications (e.g., wavelength on the order of 10 nm). The individual layers of the multilayer stack 16 are formed by conventional techniques.

It is understood that the number of bilayers in the reflective multilayer can vary depending on the desired performance in terms of wavelength and angular and temporal bandwidth. A larger number of layers will provide higher reflectivity at the cost of lower angular and temporal bandwidth. Typically, the number of layered pairs will range from about 10 to 200 and preferably from about 20 to 80. Moreover, the layer pairs will typically have a bilayer periodicity of about 5 nm to 100 nm and preferably from about 5 nm to 30 nm. By "periodicity" is meant the thickness of one bilayer. Typically, the height of the individual stack layers will range from about 0.2 to 0.8 times the total bilayer thickness and preferably from about 0.4 to 0.6 times the total bilayer thickness.

Although only preferred embodiments of the invention are specifically disclosed and described above, it will be appreciated that many modifications and variations of the present invention are possible in light of the above teachings and within the purview of the appended claims without departing from the spirit and intended scope of the invention

What is claimed is:

1. A method, for evaluating the reflection coating uniformity of an optical component that has a concave reflective optical surface, that comprises the steps of:

(a) providing an illumination source of divergent radiation having a first wavelength;

(b) positioning the optical component so that its concave reflective optical surface transforms diverging radiation from the source of divergent radiation into a converging beam at a focused point where an image of the source of divergent radiation is created;

(c) positioning a spatially imaging radiation detector far from the focused point such that substantially the entire surface of the detector is illuminated by the beam reflected from the concave surface;

(d) creating a recorded image by recording a first image that is reflected from the concave reflective optical surface to thereby geometrically map lateral positions on the concave reflective optical surface of the optical component to lateral positions of the spatially imaging detector;

(e) analyzing intensity variations across the recorded image to determine reflectivity variations across the optical surface;

(f) extrapolating reflection coating uniformity information from the reflectivity variations; and (g) optionally, repeating steps (a) through (b) one or more times as desired using divergent radiation with a different wavelength in each repetition.

2. The method of claim 1 wherein the optical component is positioned so that substantially the entire concave reflective optical surface of the optical component transforms a portion of the diverging radiation.

3. The method of claim 1 wherein step (a) comprises providing a divergent extreme ultraviolet (EUV) radiation source and wherein the spatially imaging detector is EUV radiation sensitive.

4. The method of claim 3 wherein the detector is a charge coupled detector.

5. The method of claim 1 wherein the spatially imaging detector comprises an (EUV)-sensitive scintillator plate that is re-imaged using visible light optics to a visible-light charge coupled detector.

6. The method of claim 5 wherein the scintillator plate includes a yttrium aluminum garnet (YAG) material.

7. The method of claim 5 wherein the scintillator plate includes a $Bi_4Ge_3O_{12}$ (BGO) material.

8. The method of claim 1 wherein steps (a) through (f) are repeated at least once.

9. The method of claim 1 wherein radiation from source of divergent radiation is not scanned across the concave reflective optical surface.

10. The method of claim 1 wherein step (f) is achieved by comparing said reflectivity map to a reference reflectivity map where the reference map is recorded using steps (a) through (e) from a nominally identical but independently characterized reference optic.

11. The method of claim 1 wherein the multilayer reflection film comprises alternating layers of a first material having a first refractive index and a second material having a second refractive index that is different the first refractive index.

12. The method of claim 1 wherein the multilayer reflection film comprises alternating layers of molybdenum and silicon.

13. The method of claim 1 wherein the multilayer reflection film comprises about 10 to 200 layer pairs.

14. The method of claim 1 wherein the layer pairs have a periodicity of about 5 nm to 100 nm.

15. The method of claim 11 wherein the multilayer reflection film comprises about 10 to 200 layer pairs.

16. The method of claim 11 wherein the layer pairs have a periodicity of about 5 nm to 100 nm.

17. The method of claim 12 wherein the multilayer reflection film comprises about 10 to 200 layer pairs.

18. The method of claim 12 wherein the layer pairs have a periodicity of about 5 nm to 100 nm.

19. The method of claim 1 wherein the concave reflective optical surface that transforms diverging radiation in step (b) has an area of at least 10 $mm^2$.

20. The method of claim 19 wherein the area is between 800 and 80,000 $mm^2$.

21. A method, for evaluating the coating uniformity of an optical component that has a convex or flat reflective optical surface, that comprises the steps of:
   (a) providing an illumination source of divergent radiation having a first wavelength;
   (b) positioning a concave optic which transforms the illumination source into a convergent beam;
   (c) positioning the optical component under evaluation so that its convex or flat reflective optical surface is illuminated by the convergent beam;
   (d) positioning a spatially imaging detector such that substantially the entire beam reflected from the convex or flat reflective surface is projected onto said detector;
   (e) creating a recorded image by recording a first image that is reflected from the convex or flat reflective optical surface to thereby geometrically map lateral positions on the convex or flat reflective optical surface of the optical component to the lateral positions of the spatially imaging detector;
   (f) analyzing intensity variations across the recorded image to determine the reflectivity variations across the optical surface;
   (g) extrapolating the reflection coating uniformity information from the reflectivity variations; and
   (h) optionally, repeating steps (a) through (g) one or more times as desired using divergent radiation with a different wavelength in each repetition.

22. The method of claim 21 wherein the optical component under evaluation is positioned so that substantially the entire convex or flat reflective optical surface of the optical component is illuminated by the convergent beam.

23. The method of claim 21 wherein step (a) comprises providing a divergent extreme ultraviolet (EUV) radiation source and wherein the spatially imaging detector is EUV radiation sensitive.

24. The method of claim 21 wherein the detector is a charge coupled detector.

25. The method of claim 21 wherein the spatially imaging detector comprises an EUV-sensitive scintillator plate that is re-imaged using visible light optics to a visible-light charge coupled detector.

26. The method of claim 21 wherein the scintillator plate includes a yttrium aluminum garnet (YAG) material.

27. The method of claim 21 wherein the scintillator plate includes a $Bi_4Ge_3O_{12}$ (BGO) material.

28. The method of claim 21 wherein steps (a) through (g) are repeated at least once.

29. The method of claim 21 wherein radiation from source of divergent radiation is not scanned across the concave or flat reflective optical surface.

30. The method of claim 21 wherein step (g) is achieved by comparing said reflectivity map to a reference reflectivity map where the reference map is recorded using steps (a) through (f) from a nominally identical but independently characterized reference optic.

31. The method of claim 21 wherein the multilayer reflection film comprises alternating layers of a first material having a first refractive index and a second material having a second refractive index that is different than the first refractive index.

32. The method of claim 21 wherein the multilayer reflection film comprises alternating layers of molybdenum and silicon.

33. The method of claim 21 wherein the multilayer reflection film comprises about 10 to 200 layer pairs.

34. The method of claim 21 wherein the layer pairs have a periodicity of about 5 nm to 100 nm.

35. The method of claim 31 wherein the multilayer reflection film comprises about 10 to 200 layer pairs.

36. The method of claim 31 wherein the layer pairs have a periodicity of about 5 nm to 100 nm.

37. The method of claim 32 wherein the multilayer reflection film comprises about 10 to 200 layer pairs.

38. The method of claim 32 wherein the layer pairs have a periodicity of about 5 nm to 100 nm.

39. The method of claim 21 wherein the optical component has a convex surface.

40. The method of claim 21 further comprising the steps of determining the reflectivity uniformity of the concave optic and normalizing the reflection coating uniformity information extrapolated in step (g).

41. The method of claim 40 wherein the step of determining the reflectivity uniformity of the convex or flat optic comprises evaluating the reflection coating uniformity of the concave optic which has a concave reflective optical surface, that comprises the steps of:
- (i) providing an illumination source of divergent radiation having a second wavelength;
- (ii) positioning the concave optical component so that its concave reflective optical surface transforms diverging radiation from the source of divergent radiation into a converging beam at a focused point where an image of the source of divergent radiation is created;
- (iii) positioning a spatially imaging radiation detector far field from a convergent point of the illumination source of divergent radiation;
- (iv) creating a recorded image by recording a second image that is reflected from the concave reflective optical surface to thereby geometrically map lateral positions on the concave reflective optical surface of the optical component to lateral positions of the second spatially imaging detector;
- (v) analyzing intensity variations across the recorded image to determine reflectivity variations across the concave optical surface;
- (vi) extrapolating reflection coating uniformity information from the reflectivity variations; and
- (vii) optionally, repeating steps (a) through (b) one or more times as desired using divergent radiation with a different wavelength in each repetition.

42. The method of claim 21 wherein the concave or flat optic that transforms diverging radiation in step (b) has an area of at least 10 mm$^2$ onto which the divergent radiation is illuminated in step (a).

43. The method of claim 42 wherein the area is between 800 and 80,000 mm$^2$.

* * * * *

UNITED STATES PATENT AND TRADEMARK OFFICE
CERTIFICATE OF CORRECTION

| | |
|---|---|
| PATENT NO. | : 7,016,030 B2 |
| APPLICATION NO. | : 10/689171 |
| DATED | : March 21, 2006 |
| INVENTOR(S) | : Patrick P. Naulleau |

It is certified that error appears in the above-identified patent and that said Letters Patent is hereby corrected as shown below:

At Column 2, line 39, "consists" should be --consist--.
At Column 3, line 39, "through (b)" should be --through (f)--.

At Column 7, Claim 1, line 1, "through (b)" should be --through (f)--.
At Column 7, Claim 11, lines 32 and 33, "wherein the multilayer reflective film comprises" should be --wherein the reflective optical surface comprises a multilayer reflective film that comprises--.
At Column 7, Claim 12, line 32, "claim 1" should be --claim 11--.
At Column 7, Claim 13, line 40, "claim 1" should be --claim 11--.
At Column 7, Claim 14, line 42, "claim 1" should be -claim 13--.
At Column 7, Claim 15, line 44, "claim 11" should be -claim 12--.
At Column 7, Claim 16, line 46, "claim 11" should be -claim 15--.
At Column 7, Claim 17, line 48, "claim 12" should be --claim 11 wherein the reflective optical surface is an EUV reflective surface and--.
At Column 7, Claim 18, line 50, "claim 12" should be -claim 17--.
At Column 8, Claim 29, line 39, "concave or" should be --convex or--.
At Column 8, Claim 31, lines 46 and 47, "wherein the multilayer film comprises" should be --wherein the reflective optical surface comprises a multilayer reflective film that comprises--.
At Column 8, Claim 32, line 51, "claim 21" should be -claim 31--.
At Column 8, Claim 33, line 54, "claim 21" should be --claim 31--.
At Column 8, Claim 34, line 56, "claim 21" should be --claim 33--.
At Column 8, Claim 35, line 58, "claim 31" should be -claim 32--.
At Column 8, Claim 36, line 60, "claim 31" should be --claim 35--.
At Column 8, Claim 37, line 62, "claim 32" should be --claim 31 wherein the reflective optical surface is an EUV reflective surface and--.
At Column 8, Claim 38, line 64, "claim 32" should be --claim 37--.
At Column 9, Claim 41, line 6, "convex or flat" should be --concave--.
At Column 10, Claim 41, line 10, "steps (a) through (b)" should be --steps (i) through (vi)--.

UNITED STATES PATENT AND TRADEMARK OFFICE
CERTIFICATE OF CORRECTION

PATENT NO. : 7,016,030 B2
APPLICATION NO. : 10/689171
DATED : March 21, 2006
INVENTOR(S) : Patrick P. Naulleau It is certified that error appears in the above-identified patent and that said Letters Patent is hereby corrected as shown below:

At Column 10, Claim 42, line 13, "concave or flat" should be --concave--.

Signed and Sealed this

Tenth Day of June, 2008

JON W. DUDAS
*Director of the United States Patent and Trademark Office*